United States Patent
Seibel et al.

(10) Patent No.: US 12,029,487 B2
(45) Date of Patent: Jul. 9, 2024

(54) SYSTEM AND METHOD FOR RETINA TEMPLATE MATCHING IN TELEOPHTHALMOLOGY

(71) Applicants: UNIVERSITY OF WASHINGTON, Seattle, WA (US); MAGIC LEAP, INC., Plantation, FL (US)

(72) Inventors: Eric J. Seibel, Seattle, WA (US); Chen Gong, Seattle, WA (US); Steven L Brunton, Seattle, WA (US); Nils Benjamin Erichson, Seattle, WA (US); Laura Trutoiu, Seattle, WA (US); Brian T. Schowengerdt, Seattle, WA (US)

(73) Assignee: Magic Leap, Inc., Plantation, FL (US)

( * ) Notice: Subject to any disclaimer, the term of this patent is extended or adjusted under 35 U.S.C. 154(b) by 533 days.

(21) Appl. No.: 17/295,586

(22) PCT Filed: Nov. 20, 2019

(86) PCT No.: PCT/US2019/062327
§ 371 (c)(1),
(2) Date: May 20, 2021

(87) PCT Pub. No.: WO2020/106792
PCT Pub. Date: May 28, 2020

(65) Prior Publication Data
US 2022/0015629 A1    Jan. 20, 2022

Related U.S. Application Data

(60) Provisional application No. 62/770,612, filed on Nov. 21, 2018.

(51) Int. Cl.
*A61B 3/00* (2006.01)
*A61B 3/12* (2006.01)
(Continued)

(52) U.S. Cl.
CPC .............. *A61B 3/12* (2013.01); *A61B 3/0025* (2013.01); *A61B 3/0058* (2013.01); *A61B 3/14* (2013.01);
(Continued)

(58) Field of Classification Search
CPC ....... A61B 3/12; A61B 3/0025; A61B 3/0058; A61B 3/14; G06V 40/197; G06V 40/193; G06T 3/4038
See application file for complete search history.

(56) References Cited

U.S. PATENT DOCUMENTS 6,553,152 B1 *  4/2003  Miller ................. G06V 10/754
                                                     382/294
8,879,813 B1 * 11/2014  Solanki ................ G06F 16/583
                                                     382/128
(Continued)

FOREIGN PATENT DOCUMENTS

EP         2563206        3/2013
JP      2013-525035       6/2013
(Continued)

OTHER PUBLICATIONS

Foreign Response for EP Patent Appln. No. 19886194.0 dated Jul. 15, 2022.
(Continued)

*Primary Examiner* — Khai M Nguyen
(74) *Attorney, Agent, or Firm* — Vista IP Law Group, LLP

(57) ABSTRACT

A retina image template matching method is based on the registration and comparison between the images captured with portable low-cost fundus cameras (e.g., a consumer grade camera typically incorporated into a smartphone or tablet computer) and a baseline image. The method solves the challenges posed by registering small and low-quality (Continued)

retinal template images captured with such cameras. Our method combines dimension reduction methods with a mutual information (MI) based image registration technique. In particular, principle components analysis (PCA) and optionally block PCA are used as a dimension reduction method to localize the template image coarsely to the baseline image, then the resulting displacement parameters are used to initialize the MI metric optimization for registration of the template image with the closest region of the baseline image.

20 Claims, 7 Drawing Sheets

(51) Int. Cl.
  A61B 3/14    (2006.01)
  G06T 3/4038    (2024.01)
  G06V 40/18    (2022.01)
(52) U.S. Cl.
  CPC .......... *G06T 3/4038* (2013.01); *G06V 40/193* (2022.01); *G06V 40/197* (2022.01)

(56) References Cited

U.S. PATENT DOCUMENTS

| | | | |
|---|---|---|---|
| 2002/0036750 | A1 | 3/2002 | Eberl et al. |
| 2007/0252951 | A1 | 11/2007 | Hammer et al. |
| 2009/0123044 | A1 | 5/2009 | Huang et al. |
| 2010/0080425 | A1* | 4/2010 | Bebis ............... G06V 40/1353 382/125 |
| 2012/0229764 | A1 | 9/2012 | Tomatsu et al. |
| 2013/0208241 | A1 | 8/2013 | Lawson et al. |
| 2014/0198300 | A1 | 7/2014 | Goto et al. |
| 2015/0110348 | A1* | 4/2015 | Solanki ............... G06V 10/50 382/103 |
| 2016/0270656 | A1 | 9/2016 | Samec et al. |
| 2017/0076136 | A1 | 3/2017 | Xue et al. |

FOREIGN PATENT DOCUMENTS

| | | |
|---|---|---|
| JP | 2014-505952 | 3/2014 |
| WO | WO 2011/139895 | 11/2011 |
| WO | WO 2012/109712 | 8/2012 |
| WO | WO 2018/125812 | 7/2018 |

OTHER PUBLICATIONS

Foreign OA for JP Patent Appln. No. 2021-527904 dated Oct. 2, 2023 (with English translation).
Extended European Search Report for EP Patent Appln. No. 19886194.0 dated Dec. 8, 2021.
PCT International Search Report and Written Opinion for International Appln. No. PCT/US2019/062327, forms PCT/ISA/210, 220, and 237, dated Mar. 3, 2020 (16 pages).
Foreign OA for CN Patent Appln. No. 201980076416.2 dated Sep. 26, 2023.
Foreign Response for CN Patent Appln. No. 201980076416.2 dated Jan. 12, 2024.
Baghaie, A. et al., "Sparse and low rank decomposition based batch image alignment for speckle reduction of retinal OCT images," in Proc. IEEE 12th Int. Symp. Biomed. Imag. (ISBI), Apr. 2015, pp. 226-230.
Bouwmans, T. et al., "On the applications of robust PCA in image and video processing," Proc. IEEE, vol. 106, No. 8, pp. 1427-1457, Aug. 2018.
Candès, E. J. et al., "Robust principal component analysis?" J. ACM, vol. 58, No. 3, pp. 11-37, May 2011.
Cideciyan, A. V. "Registration of ocular fundus images: An algorithm using cross-correlation of triple invariant image descriptors," IEEE Eng. Med. Biol. Mag., vol. 14, No. 1, pp. 52-58, Jan./Feb. 1995.
Dai, X. et al., "Trend analysis of fragmented time series for mhealth apps: Hypothesis testing based adaptive spline filtering method with importance weighting," IEEE Access, vol. 5, pp. 27767-27776, 2017.
Erichson, N. B. et al., "Randomized matrix decompositions using R," arXiv, 2016, https://arxiv.org/abs/1608.02148.
Erichson, N. B. et al., "Randomized nonnegative matrix factorization," Pattern Recognit. Lett., vol. 104, pp. 1-7, Mar. 2018.
Figueiredo, I. N. et al., "Automated lesion detectors in retinal fundus images," Comput. Biol. Med., vol. 66, pp. 47-65, Nov. 2015.
Figueiredo, I. N. et al., "Automated retina identification based on multiscale elastic registration," Comput. Biol. Med., vol. 79, pp. 130-143, Dec. 2016.
Figueiredo, I. N. et al., "Pattern classes in retinal fundus images based on function norms," in Proc. Int. Symp. Comput. Modeling Objects Represented Images. Cham, Switzerland: Springer, 2014, pp. 95-105.
Fink, W. et al., "Smart ophthalmics: The future in tele-ophthalmology has arrived," Proc. SPIE, vol. 9836, May 2016, Art. No. 98360W.
Fitzpatrick, J. M. et al., "Predicting error in rigid-body point-based registration," IEEE Trans. Med. Imag., vol. 17, No. 5, pp. 694-702, Oct. 1998.
Friston, K. J. et al., "Spatial registration and normalization of images," Hum. Brain Mapping, vol. 3, No. 3, pp. 165-189, Mar. 1995.
Fu, Y. et al., "Automatic detection of longitudinal changes for retinal fundus images based on low-rank decomposition," J. Med. Imag. Health Informat., vol. 8, No. 2, pp. 284-294, Feb. 2018.
Gong, C. et al., "RetinaMatch: Efficient Template Matching of Retina Images for Teleophthalmology" IEEE Transactions on Medical Imaging, vol. 38, No. 8, Aug. 2019, 1993-2004.
Gong, C. et al., "Measurement of retinal vessel width in tele-ophthalmology for mobile health monitoring," Investigative Ophthalmology Vis. Sci., vol. 59, No. 9, p. 4624, Jul. 2018.
Gulshan, V. et al., "Development and validation of a deep learning algorithm for detection of diabetic retinopathy in retinal fundus photographs," J. Amer. Med. Assoc., vol. 316, No. 22, pp. 2402-2410, 2016.
Halko, N. et al., "Finding structure with randomness: Probabilistic algorithms for constructing approximate matrix decompositions," SIAM Rev., vol. 53, No. 2, pp. 217-288, 2011.
Hernandez-Matas, C. et al., "Retinal image registration based on keypoint correspondences, spherical eye modeling and camera pose estimation," in Proc. 37th Annu. Int. Conf. IEEE Eng. Med. Biol. Soc. (EMBC), Aug. 2015, pp. 5650-5654.
Hotelling, H. "Analysis of a complex of statistical variables into principal components," J. Educ. Psychol., vol. 24, No. 6, p. 417, 1933.
Hu, D. et al., "Semiautonomous image-guided brain tumour resection using an integrated robotic system: A bench-top study," Int. J. Med. Robot. Comput. Assist. Surg., vol. 14, No. 1, p. e1872, Feb. 2018.
Kawasaki, R. et al., "Retinal vessel diameters and risk of hypertension: The multiethnic study of atherosclerosis.," J. Hypertension, vol. 27, No. 12, pp. 93-2386, Dec. 2009.
Kutz, J. N. et al., Dynamic Mode Decomposition: Data-Driven Modeling of Complex Systems, vol. 149. Philadelphia, PA, USA: SIAM, 2016.
Liberty, E. et al., "Randomized algorithms for the low-rank approximation of matrices," Proc. Nat. Acad. Sci. USA, vol. 104, No. 51, pp. 20167-20172, Dec. 2007.
Ludwig, C. A. "The future of automated mobile eye diagnosis," Byers Eye Inst., Stanford Univ. School Med., Palo Alto, CA, USA, Tech. Rep. Journal MTM 5:2:44-50, 2016. doi: 10.7309/jmtm.5.2.7.
Mattes, D. et al., "PET-CT image registration in the chest using free-form deformations," IEEE Trans. Med. Imag., vol. 22, No. 1, pp. 120-128, Jan. 2003.

(56) References Cited

OTHER PUBLICATIONS

Mora, A. D. et al., "A template matching technique for artifacts detection in retinal images," in Proc. 8th Int. Symp. Image Signal Process. Anal. (ISPA), Sep. 2013, pp. 717-722.

Morel, J.-M. et al., "ASIFT: A new framework for fully affine invariant image comparison," SIAM J. Imag. Sci., vol. 2, No. 2, pp. 438-469, 2009.

Panwar, N. et al., "Fundus photography in the 21st century—A review of recent technological advances and their implications for worldwide healthcare," Telemed. e-Health, vol. 22, No. 3, pp. 198-208, Mar. 2016.

Pearson, F. R. S. K. "LIII. On lines and planes of closest fit to systems of points in space," London, Edinburgh, Dublin Philosoph. Mag. J. Sci., vol. 2, No. 11, pp. 559-572, 1901.

Roesch, K. et al., "Automated retinal imaging and trend analysis—A tool for health monitoring," Clin. Ophthalmology, vol. 11, pp. 1015-1020, May 2017.

Schölkopf, B. et al., "Kernel principal component analysis," in Proc. Int. Conf. Artif. Neural Netw. New York, NY, USA: Springer, Oct. 1997, pp. 583-588.

Shi, L. et al., "Telemedicine for detecting diabetic retinopathy: A systematic review and meta-analysis," Brit. J. Ophthalmology, vol. 99, No. 6, pp. 823-831, Jun. 2015.

Sofka, M. et al., "Retinal vessel centerline extraction using multiscale matched filters, confidence and edge measures," IEEE Trans. Med. Imag., vol. 25, No. 12, pp. 1531-1546, Dec. 2006.

Stewart, C. V. et al., "The dual-bootstrap iterative closest point algorithm with application to retinal image registration," IEEE Trans. Med. Imag., vol. 22, No. 11, pp. 1379-1394, Nov. 2003.

Tenenbaum, J. B. et al., "A global geometric framework for nonlinear dimensionality reduction," Science, vol. 290, No. 5500, pp. 2319-2323, Dec. 2000.

The STARE Project. Structured Analysis of the Retina. Accessed: May 15, 2018. http://www.ces.clemson.edu/~ahoover/stare/.

Thevenaz, P. et al., "Spline pyramids for intermodal image registration using mutual information," Proc. SPIE, vol. 3169, Oct. 1997, pp. 236-248.

Tsai, C. L. et al., "The edge-driven dual-bootstrap iterative closest point algorithm for registration of multimodal fluorescein angiogram sequence," IEEE Trans. Med. Imag., vol. 29, No. 3, pp. 636-649, Mar. 2010.

Van Rijn, L. J. "Torsional eye movements in humans," Investigational New Drugs—Invest New Drug, Jan. 1994.

Walter, T. et al., "A contribution of image processing to the diagnosis of diabetic retinopathy-detection of exudates in color fundus images of the human retina," IEEE Trans. Med. Image, vol. 21, No. 10, pp. 1236-1243, Oct. 2002.

Wang, G. et al., "Robust point matching method for multimodal retinal image registration," Biomed. Signal Process. Control, vol. 19, pp. 68-76, May 2015.

Wang, S. et al., "Human visual system-based fundus image quality assessment of portable fundus camera photographs," IEEE Trans. Med. Imag., vol. 35, No. 4, pp. 1046-1055, Apr. 2016.

Wang, Y. et al., "Automatic fundus images mosaic based on SIFT feature," in Proc. 3rd Int. Congr. Image Signal Process. (CISP), vol. 6, Oct. 2010, pp. 2747-2751.

Xu, J. et al., "Optic disk feature extraction via modified deformable model technique for glaucoma analysis," Pattern Recognit., vol. 40, No. 7, pp. 2063-2076, Jul. 2007.

Xu, X. et al., "Smartphone-based accurate analysis of retinal vasculature towards point-of-care diagnostics," Sci. Rep., vol. 6, Oct. 2016, Art. No. 34603.

Yu, H. et al., "Fast localization and segmentation of optic disk in retinal images using directional matched filtering and level sets," IEEE Trans. Inf. Technol. Biomed., vol. 16, No. 4, pp. 644-657, Jul. 2012.

Yusuf, I. H. et al., "Non-contact ultra-widefield retinal imaging of infants with suspected abusive head trauma," Eye, vol. 31, No. 3, p. 353, Mar. 2017.

Zhang X. et al., "Exudate detection in color retinal images for mass screening of diabetic retinopathy," Med. Image Anal., vol. 18, No. 7, pp. 1026-1043, Oct. 2014.

Zhu, Y.-M. "Mutual information-based registration of temporal and stereo retinal images using constrained optimization," Comput. Methods Programs Biomed., vol. 86, No. 3, pp. 210-215, Jun. 2007.

Foreign OA for JP Patent Appln. No. 2021-527904 dated Mar. 4, 2024.

Foreign Exam Report for EP Patent Appln. No. 19886194.0 dated Feb. 26, 2024.

Foreign OA for CN Patent Appln. No. 201980076416.2 dated Mar. 18, 2024 (with English translation).

Foreign Response for CN Patent Appln. No. 201980076416.2 dated May 15, 2024.

* cited by examiner

SYSTEM AND METHOD FOR RETINA TEMPLATE MATCHING IN TELEOPHTHALMOLOGY

PRIORITY

This application claims priority to PCT Application No. PCT/US2019/062327, filed on Nov. 20, 2019, entitled "SYSTEM AND METHOD FOR RETINA TEMPLATE MATCHING IN TELEOPHTHALMOLOGY," which claims priority to U.S. Provisional application Ser. No. 62/770,612, filed Nov. 21, 2018, The contents of the aforementioned patent applications are hereby expressly and fully incorporated by reference into the present application.

FIELD

This disclosure relates to systems and methods for matching and registering a small field of view image of the fundus to a previously obtained baseline, wide field of view image. The baseline image can take the form of a wide field of view fundus image obtained by a fundus camera, e.g., of the type found in an eye clinic. Alternatively, the baseline image could be a composite or mosaic image of some or all of the fundus from previously obtained stitched or registered images. The term "baseline image" is intended to be interpreted to cover either situation.

In this document, the term "template" or alternatively "template image" is used to refer to the small field of view image to be matched and registered with the baseline image. "Teleophthalmology" is used to refer to the practice of monitoring of retinal health and visual performance of a patient remotely, i.e., with the patient not physically present in the traditional eye clinic. The monitoring could be done by the patient with the aid of one of the portable fundus cameras of this disclosure and without direct input from their eye doctor, or by the remotely-located patient and their eye doctor using computer networks to share information and fundus images.

BACKGROUND

Recently, teleophthalmology has been facilitated by the ability of consumer grade cameras, such as those found in smartphones, to obtain images of the fundus. Images of the fundus captured by a person in the home setting can be sent over computer networks and studied by the person's eye doctor and thereby allow the monitoring of the health of the eye without the person physically making a trip to the eye clinic. In addition, the emerging virtual and mixed reality sector may enable new teleophthalmology scenarios for head-worn eye imaging and monitoring. By combining these emerging technologies with advanced image processing algorithms, long-term or longitudinal monitoring of health can be provided for the first time by imaging the retina in everyday life of the person.

Examples of these new portable fundus camera (PFC) systems are commercially available from many sources, or else described in the literature, including devices which are designed to be combined with a smartphone. See e.g., U.S. Pat. No. 8,836,778, a digital fundus camera product incorporating a smartphone, known as "D-Eye" see https://www.d-eyecare.com, and RN Maamari, et al., *A mobile phone-based retinal camera for portable wide field imaging.* British Journal of Ophthalmology98(4):438 (2014). Other portable laser-based imaging systems are forthcoming as they are becoming the mainstay of clinical ophthalmic imaging, which are portable scanning laser ophthalmoscopes (PSLO), see U.S. Pat. No. 6,758,564, and portable optical coherence Tomography (POCT) systems, see U.S. Pat. No. 7,648,242. Unlike fundus cameras that use visible light imaging, these laser-based retinal imaging systems typically use infrared wavelengths of light. Additionally, augmented reality headsets can be adapted with cameras and ancillary optical components to image the fundus. The term "portable fundus camera" is intended to refer to any portable, e.g., hand-held or head-worn device designed or adapted to be used to capture images of the fundus, and is interpreted to encompass the devices described above and in the above patent and scientific literature.

Retinal template matching and registration is an important challenge in teleophthalmology with these low-cost and portable imaging devices. It allows the regular screening and comparison of retina changes by matching the template images captured with low-quality imaging devices onto a previously obtained large Field of View (FOV) baseline image. Changes between the current and prior images can indicate disease progression or improvement, or the onset of disease. Typically, the images from such low-cost devices are low in quality, defined as generally having a much smaller FOV because the pupil is not being dilated at the eye clinic. Furthermore, the lower-cost detectors and lower power light sources acquire images with untrained users having many different quality degradations.

These attributes of new portable retinal imaging devices present major challenges to matching the small FOV images (i.e., "templates") to the large FOV or panoramic baseline image of the retina for determining changes in health status of the user.

Retina image registration approaches can be classified into area-based and feature-based methods. Feature based methods optimize the correspondence between extracted salient objects in retina images. See e.g., C. V. Stewart, et al., "*The dual-bootstrap iterative closest point algorithm with application to retinal image registration,*" IEEE transactions on medical imaging, vol. 22, no. 11, pp. 1379-1394, 2003. Typically, bifurcations, fovea, and the optic disc are common features used for retinal image registration. A small FOV template has little probability of containing specific landmarks on the retina, thus the fovea and optic disc are not applicable. Vascular bifurcations are more common, while similarly, the small amount of bifurcations in the template cannot form the basis of a robust registration. Besides, the extraction of the vascular network in poor quality images is difficult. It can cause ambiguous vascular directions when labelling the bifurcations. General feature point based approaches are also implemented in retina registration, such as SIFT-based (see Y. Wang, et al. "*Automatic fundus images mosaic based on sift feature,*" in Image and Signal Processing (LISP), 2010 3rd International Congress on, vol. 6. IEEE, 2010, pp. 2747-2751; C.-L. Tsai, et al., "*The edge-driven dual-bootstrap iterative closest point algorithm for registration of multimodal fluorescein angiogram sequence,*" IEEE transactions on medical imaging, vol. 29, no. 3, pp. 636-649, 2010, and SURFbased methods (G. Wang, et al., "*Robust point matching method for multimodal retinal image registration,*" Biomedical Signal Processing and Control, vol. 19, pp. 68-76, (2015), C. Hernandez-Matas, et al., "*Retinal image registration based on keypoint correspondences, spherical eye modeling and camera pose estimation,*" in Engineering in Medicine and Biology Society (EMBC), 2015 37th Annual International Conference of the IEEE, IEEE, 2015, pp. 5650-5654. These approaches can register the images in complex scenarios and are computationally efficient. They assume the feature point pairs can be reliably detected and matched to estimate the transformation. Although feasible in most cases, the process can fail on low-quality retina images without enough distinct features.

Area-based approaches match the intensity differences of an image pair under a similarity measure, such as SSD (sum of squared differences) K. J. Friston, et al., "*Spatial registration and normalization of images,*" Human brain mapping, vol. 3, no. 3, pp. 165-189, 1995, CC (Cross-Correlation) (see A. V. Cideciyan, "*Registration of ocular fundus images: an algorithm using cross-correlation of triple invariant image descriptors,*" IEEE Engineering in Medicine and Biology Magazine, vol. 14, no. 1, pp. 52-58, 1995) and MI (mutual information) (see Y.-M. Zhu, "*Mutual information-based registration of temporal and stereo retinal images using constrained optimization,*" Computer methods and programs in biomedicine, vol. 86, no. 3, pp. 210-215, (2007)), then optimize the similarity measure by searching in the transformation space. Avoiding pixel level feature detection, such approaches are more robust to poor quality images than feature-based approaches. However, retina images with sparse features and similar backgrounds are likely to lead the optimization into local extrema. Additionally, when the size difference between the template and full image is too large, the registration with mutual information (MI, described below) can be computationally very expensive.

The small retina template images with low quality result in homogeneous nonvascular surfaces which are similar to homogeneous nonvascular surfaces which are present in other areas, which makes the current retina image registration methods not applicable. Overcoming the challenges in retina template matching, a method is disclosed in this document for matching templates images from low-cost imaging devices onto a baseline image. This approach is an improvement over the area-based method with a MI metric, since it is more reliable to achieve accurate and robust template matching near the alignment position. This is also the first time that a retina template matching method is proposed in teleophthalmology for remote retina health monitoring.

SUMMARY

A retina image template matching method, referred to herein as "RetinaMatch," which is particularly suitable for remote retina health monitoring is disclosed. The methods of this disclosure can be of use especially in rural areas where access to clinics and regular eye care is limited by distance and the difficulty and cost of travel. The retina monitoring is based on the registration and comparison between the images remotely captured with portable low-cost fundus cameras (PLFCs, e.g., a consumer grade camera such as a camera incorporated into a smartphone or tablet computer) and a baseline image. RetinaMatch solves the challenges posed by registering small and low-quality retinal template images captured with such cameras.

Our method combines dimension reduction methods with a mutual information (MI) based image registration technique. In particular, principle components analysis (PCA) and optionally block PCA are used as a dimension reduction method to localize the template image coarsely to the baseline image, then the resulting displacement parameters are used to initialize the MI metric optimization for registration of the template image with the closest region of the baseline image. With the initialization near the optimal position, the transformation search space for optimization is narrowed significantly.

We also disclose methods of constructing a panorama or mosaic image from a set of individual template images. Dimension reduction can also be implemented in a process of template image mosaicking, which accelerates the matching of overlapped image patches. Additionally, a new image mosaicking method is presented using the coarse alignment methodology discussed herein. PCA is used to determine the adjacent images to be stitched and MI-based registration is applied on adjacent image pairs.

In one specific embodiment, a method is disclosed for monitoring a retina of a subject. The method includes the steps of (a) obtaining a set of small field of view (FOV) ("template") images of the retina captured with a portable fundus camera, (b) matching the template images to a previously captured wide FOV baseline image of the retina using dimension reduction for the baseline image and template images and a mutual information registration method for registering the template images to portions of the baseline image, and (c) comparing the registered set of template images to the baseline image to detect any differences between the registered set of template images and the baseline image, wherein any differences indicate occurrence or change of a condition of the retina or the subject. For example, the differences can indicate progression (e.g., a worsening or improvement) of a disease or condition, subject response to treatment or therapy, onset of an eye disease such as glaucoma, or the onset or progression of disease generally in the subject, such as diabetes. The change can be part of a progression, or alternatively independent of any detected trend or progression. Example applications of the method in the context of teleophthalmology are explained in detail later in this document.

In another aspect, a computer-implemented method of registering a narrow field of view template image to a wide field of view, previously obtained, baseline image is disclosed. As explained previously, the baseline image could be a single image for example obtained from a conventional fundus camera in an eye clinic, or a mosaic of previously obtained images. The method includes step of:

(1) cropping the baseline image into a multitude of smaller offset target images;
(2) applying a dimension reduction method to map the offset target images to a representation in a lower dimensional space;
(3) mapping the template image into the lower dimensional space using the dimension reduction method;
(4) finding the corresponding nearest target image for the template image in the lower dimensional space;
(5) registering the template image to the nearest target image;
(6) identifying the location of the template image on the baseline image based on the position of the nearest target image; and
(7) registering the template image to the baseline image at the location identified in step (6).

In still another aspect, a novel portable fundus camera is contemplated, which includes a camera, an optical device coupled to the camera facilitating collecting images of the interior of the eye, a processing unit and a memory storing instructions for a processing unit, the instructions in the form of code for performing the procedure recited the previous paragraph. In this embodiment the portable fundus camera includes the software for matching the template to the baseline image. In one configuration, the camera is incorporated in a smartphone or tablet computer. In another configuration, the camera is incorporated into a head-mounted virtual or augmented reality unit.

In still another aspect, a method for assembling a wide field of view mosaic image from a multitude of small field of view images is disclosed. The method includes steps of:
 (a) mapping the small field of view images $X=X_1, X_2, \ldots X_n$ to a lower dimensional space using Principal Component Analysis (PCA);
 (b) for each of the small field of view images $X_i$:
  (1) finding the nearest neighbor(s) small field of view images by minimizing the feature distance $\Delta(Z_i, Z_j)$ where $Z_i, Z_j$ represent principal components of the ith and jth images $X_i$ and $X_j$; and
  (2) computing the Mutual Information (MI) between each $X_i$ and the nearest neighbor(s) found in step (1) and designating as the adjacent image that image with the highest MI; and
 (c) aligning at least some of the adjacent images determined from step (b) (2)) using a MI-based registration method.

BRIEF DESCRIPTION OF THE DRAWINGS

The appended drawing figures are offered by way of example and not limitation of currently preferred embodiments of this disclosure.

DETAILED DESCRIPTION

This document discloses an efficient and accurate retinal matching system and method combining dimension reduction and mutual information (MI), we refer to the technique here as RetinaMatch. By way of overview, the dimension reduction initializes the MI optimization as a coarse localization process, which narrows the optimization domain and avoids local optima. The disclosed system and method outperforms to-date existing template matching solutions. In addition, we disclose a system and method for image mosaicking with area-based registration, providing a robust approach which may be used when the feature-based methods fail. To the best of our knowledge, this is the first template matching technique for retina images with small template images from unconstrained retinal areas.

Our approach is an improvement over the area-based matching methods with MI metric, since it is more reliable to achieve accurate and robust template matching near the alignment position. One unique aspect of our approach is that we combine dimension reduction methods with the MI-based registration to reduce the interference of local extrema and improve the matching efficiency.

Figure 1:
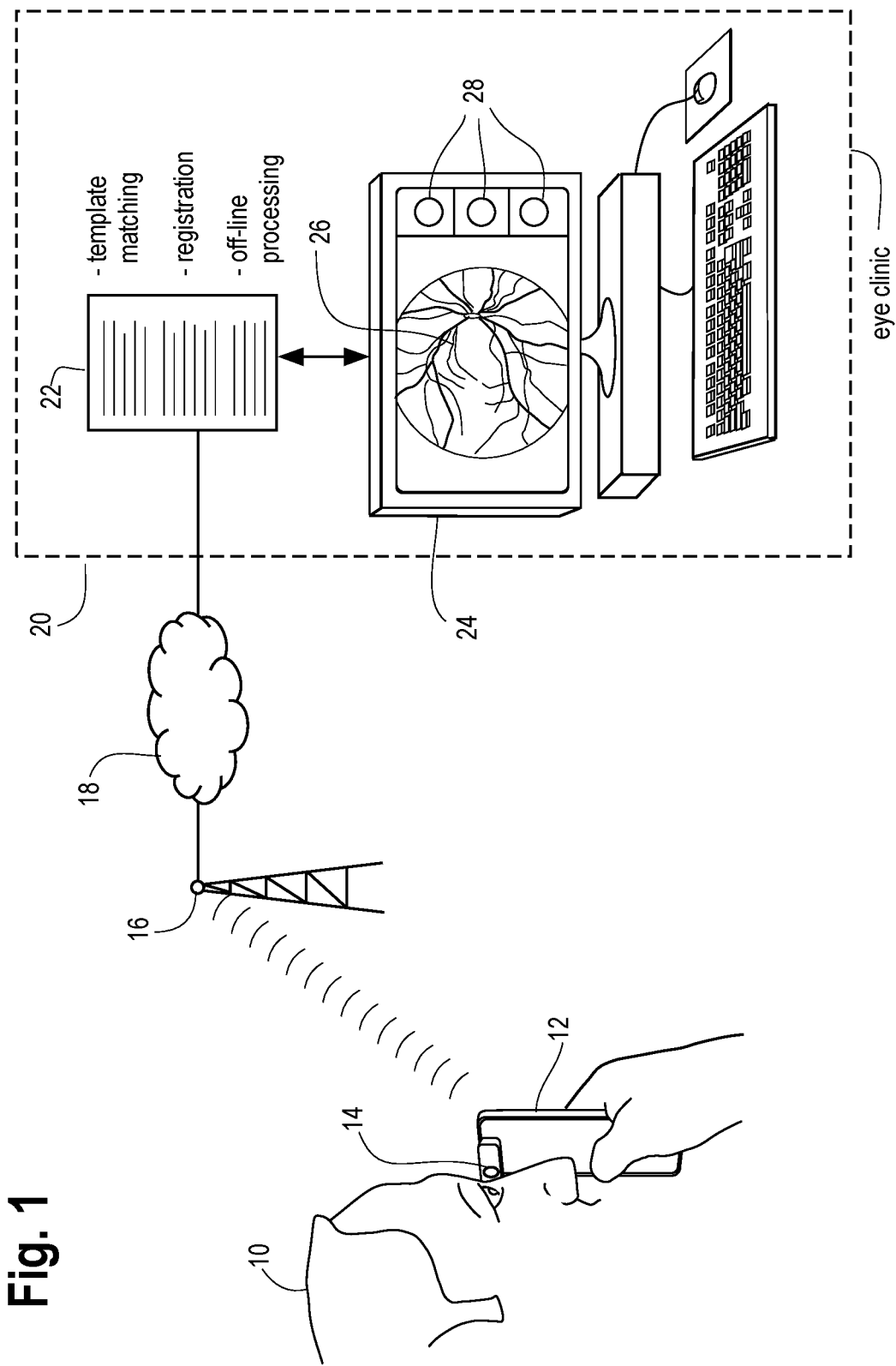
FIG. 1 is an illustration of one example of a teleophthalmology environment in which the features of this disclosure can be practiced.

An example of the practical use of our method in monitoring the retina in a teleophthalmology setting is shown in FIG. 1. A subject 10 has a portable fundus camera, in this example in the form of a smartphone 12 with ancillary apparatus 14 adapted for imaging the eye (for example the D-eye device). The subject's eye need not be chemically dilated. The subject 10 holds the camera 12 and apparatus 14 up to their eye and captures a series of small field of view images perhaps 30 or 50 in all. In one configuration, the smartphone 12 includes a processing unit and memory storing instructions for implementing the template matching procedure of FIG. 2 (discussed below). In particular, the smartphone captures a series of template images, registers them to a baseline image stored in the phone, and conducts a comparison between the two to determine if differences exist, where the differences can indicate an occurrence or change of a condition of the retina in the interim. The changes can be reported to the subject 10, e.g., via a template matching app that performs the comparison. In the event that some condition has developed or worsened based on the comparison, the subject can alert their eye doctor and/or send the mosaicked template images via the cellular network 16, internet 18 and to the eye clinic. The eye clinic includes a workstation 24 where the eye doctor can view the currently obtained mosaicked image 26 as well as stored prior mosaicked or baseline images 28 and make comparisons, make measurements of particular retinal features, etc., and coordinate treatment or further evaluation of the subject. While the above description indicates that the subject 10 could be a patient, that is not necessarily the case and could be any user, e.g., a user of a virtual reality (VR) headset, see the discussion in the applications section below.

It is also contemplated that the template images captured by the smartphone 12 could be sent over the network 16, 18 to a computing system 22 in the eye clinic and the processing steps of FIG. 2 could be performed in the eye clinic computing system 22, including the off-line processing steps (see discussion below), template matching and registration of template images to the baseline image. This configuration may be suitable when the portable fundus camera used by the patient 10 has limited processing power. The portable fundus camera may have the capability to connect to a computer network to share the images with the eye clinic, either directly (e.g., using WIFI) or the images can be otherwise downloaded to another device such as a personal computer or smartphone and then transmitted to the eye clinic for processing.

Specific examples of the applications of the retinal template matching in a teleophthalmology setting will be discussed at length later in this document.

With the above description in mind, one of the principal aspects of this disclosure is application of dimension reduction methods with the MI-based registration to reduce the inference of local extrema and improve the matching efficiency.

Figure 2:
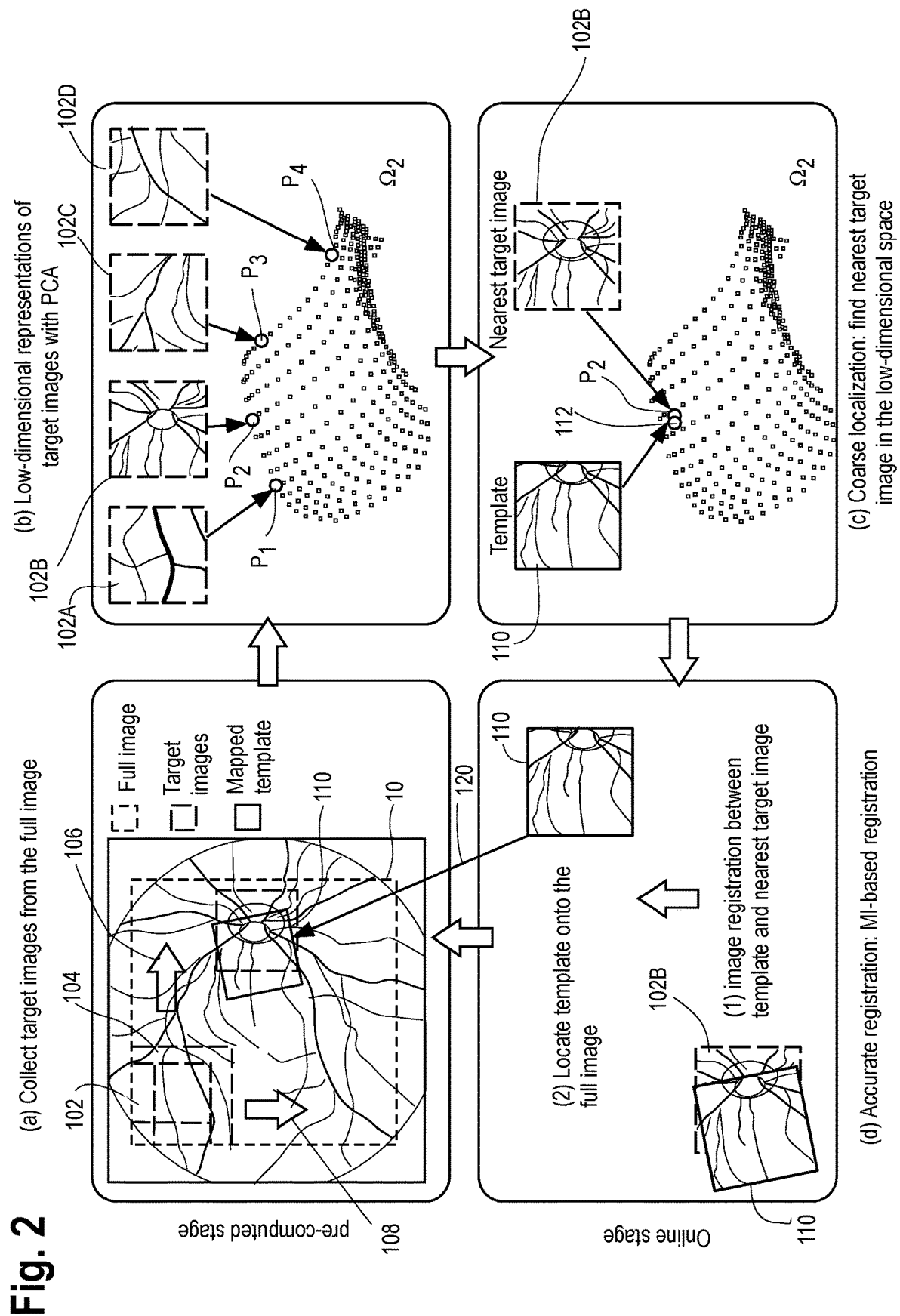
FIG. 2 illustrates the overview of our template matching method, including four panels or processing steps:
 (a) create a multitude of offset target images from a full/baseline image;
 (b) create low-dimensional representations of each of the target images using PCA;
 (c) perform coarse localization of the template image: find the nearest target image in the low-dimensional space; and
 (d) MI-based registration of the template and the nearest target image, and locate the template image onto the baseline image.

FIG. 2 illustrates an overview and schematic of the retinal template matching method shown in four panels from (a) to (d). In panel (a) a wide-FOV full or baseline image 10 is sampled, or cropped, into many overlapping or offset "target" images 102, 104, etc. The arrows 106 and 108 indicate the cropping or creation of target images occurs in the X and Y directions such that the full image 10 shown in the dashed lines is cropped into offset, smaller target images similar to images 102 and 104. In panel (b), each target image (shown as images 102A, 102B, 102C 102D etc.) is mapped into a low-dimensional space $\Omega_2$ according to its positional relationship using PCA. The dots P1, P2, P3, P4 show the low dimensional representations of the images 102A, 102B, 102C 102D in the low dimensional space. (It will be understood that the panel (b) shows only a two dimensional space but in practice the representations may be made in a low dimensional space of say 20 dimensions, depending on the implementation of PCA.) In panel (c) a small field of view template image 110 is also mapped into this space using PCA (represented by the dot 112) and its nearest target image (image 102B, represented by the dot P2) is found. In panel (d), the template image 110 is registered to its nearest target image 102B with mutual information (MI). Specifically, in panel (c) the principal component analysis (PCA) and block PCA are used to localize the template image 110 coarsely, then the resulting displacement parameters are used to initialize the MI metric optimization for the registration procedure of panel (d). The initial parameters provided by the coarse localization are in the convergence domain of the MI metric. With the initialization near the optimal position, the transformation search space for optimization is narrowed significantly. The PCA computations shown in panels (b) and (c) are accelerated with randomized methods, which improve the coarse localization efficiency. As shown in panel (d), the template 110 is located or matched on to the full or baseline image 100 using the information of the location of the nearest target image 102B.

The process of FIG. 2 panels (c) and (d) repeats for all the template images 110 that are captured; they are all registered to their nearest target image and then located onto the baseline image. After completion of the panel (d) process for all template images 110 a comparison between the registered template images and baseline image can then be performed. Additionally, the template images can be mosaicked into a new baseline image such that when a subsequent set of template images are obtained they can be compared to the updated baseline image created from a previous iteration of the procedure of FIG. 2.

Figure 5:
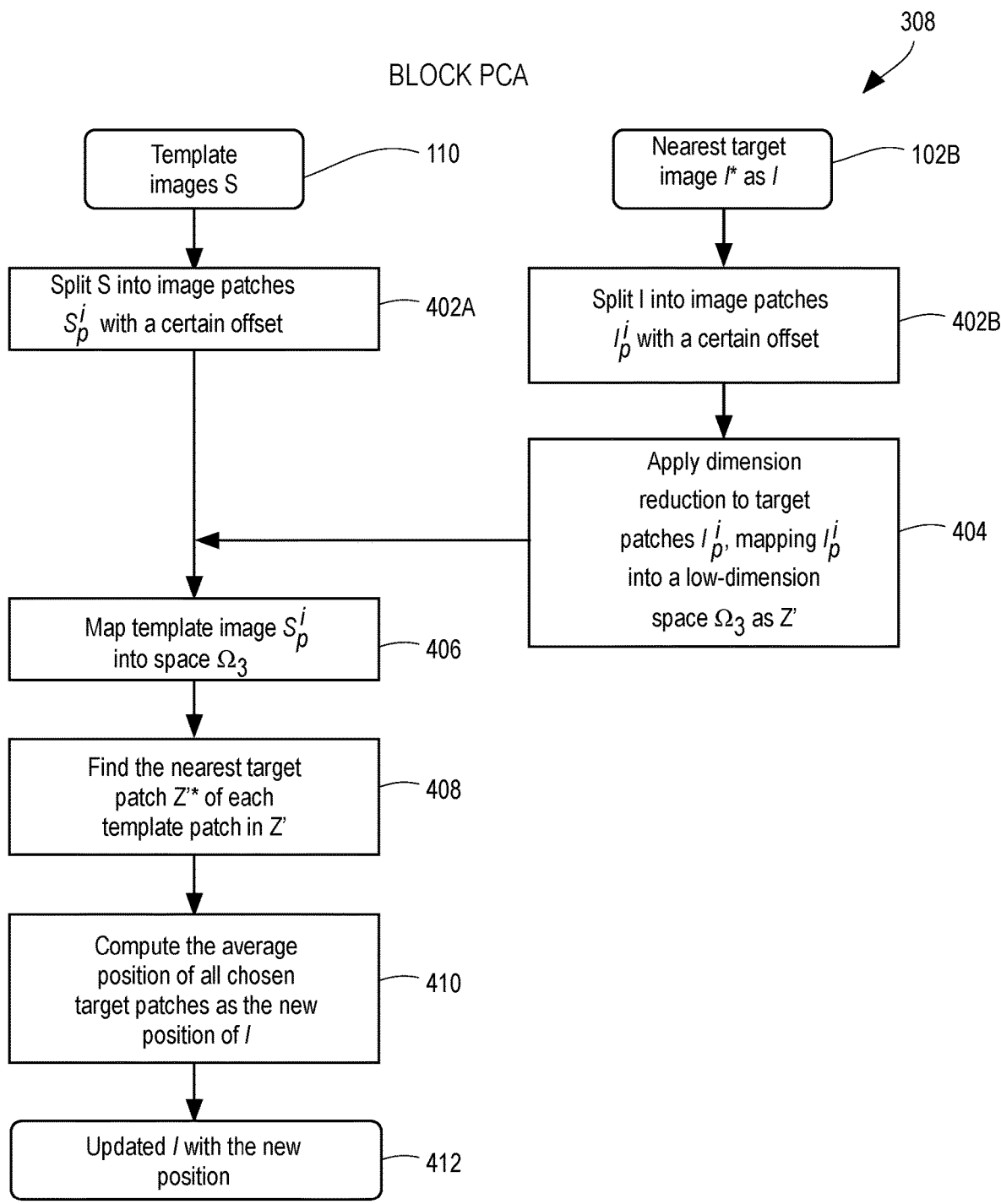
FIG. 5 is a flow chart of the block PCA step 308 in FIG. 4.

The procedures shown in panels (a) and (b) of FIG. 2 can be pre-processed when the full (or baseline) image is obtained, while panels (c) and (d) could be considered as an "on-line" stage when the template images are acquired in real time, or alternatively come into the clinic from the patient in a remote location. The procedures of panels (a)-(d) could be all executed in the processing unit of the portable fundus camera, smartphone, etc. that is used to acquire the template images. Alternatively, some or all of the processing steps of panels (a)-(d) could be done on a remote computing platform, such as for example a workstation in an eye clinic as shown in FIG. 1. The schematic of FIG. 2 describes the method without using the improvement of block PCA for finding the nearest target image. FIG. 5 shows the details of block PCA and will be discussed in detail below.

Figure 3:
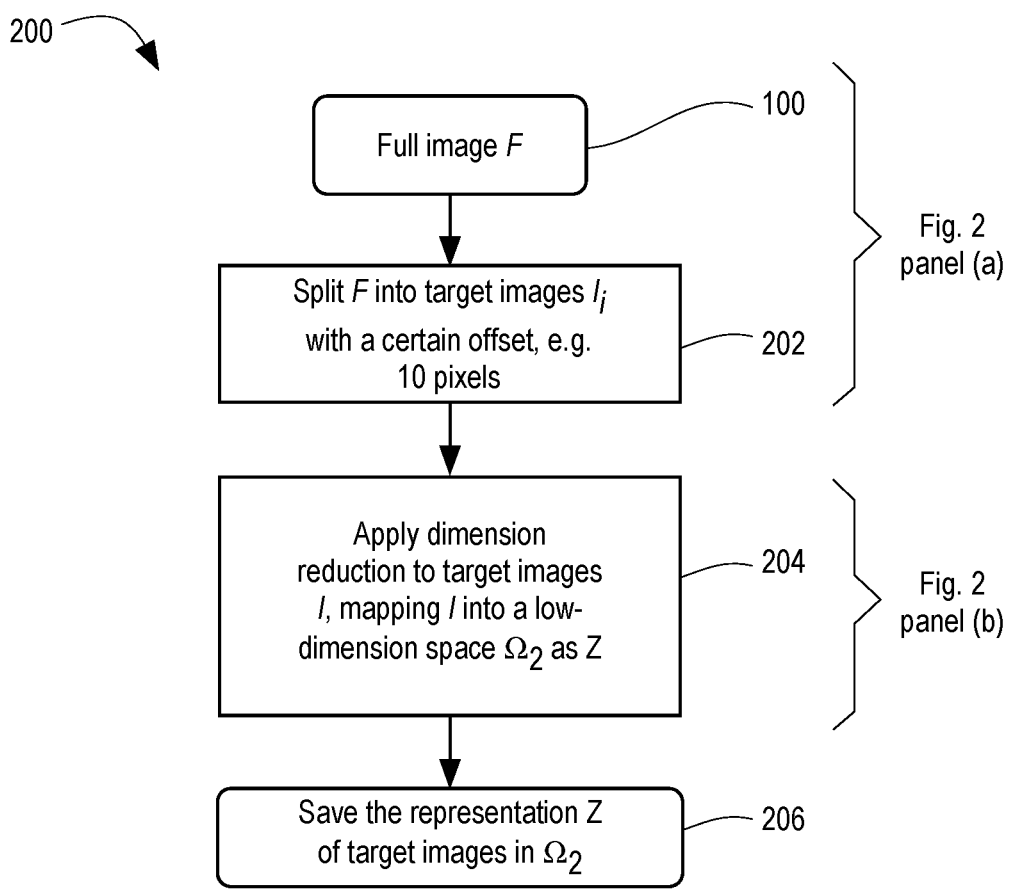
FIG. 3 is a flow chart of the sequence of processing instructions representing panels (a) and (b) of FIG. 2. These processing steps can be done in a pre-computation or "off-line" manner, i.e., in advance of the template matching and registration steps of panels (c) and (d) of FIG. 2.
Figure 4:
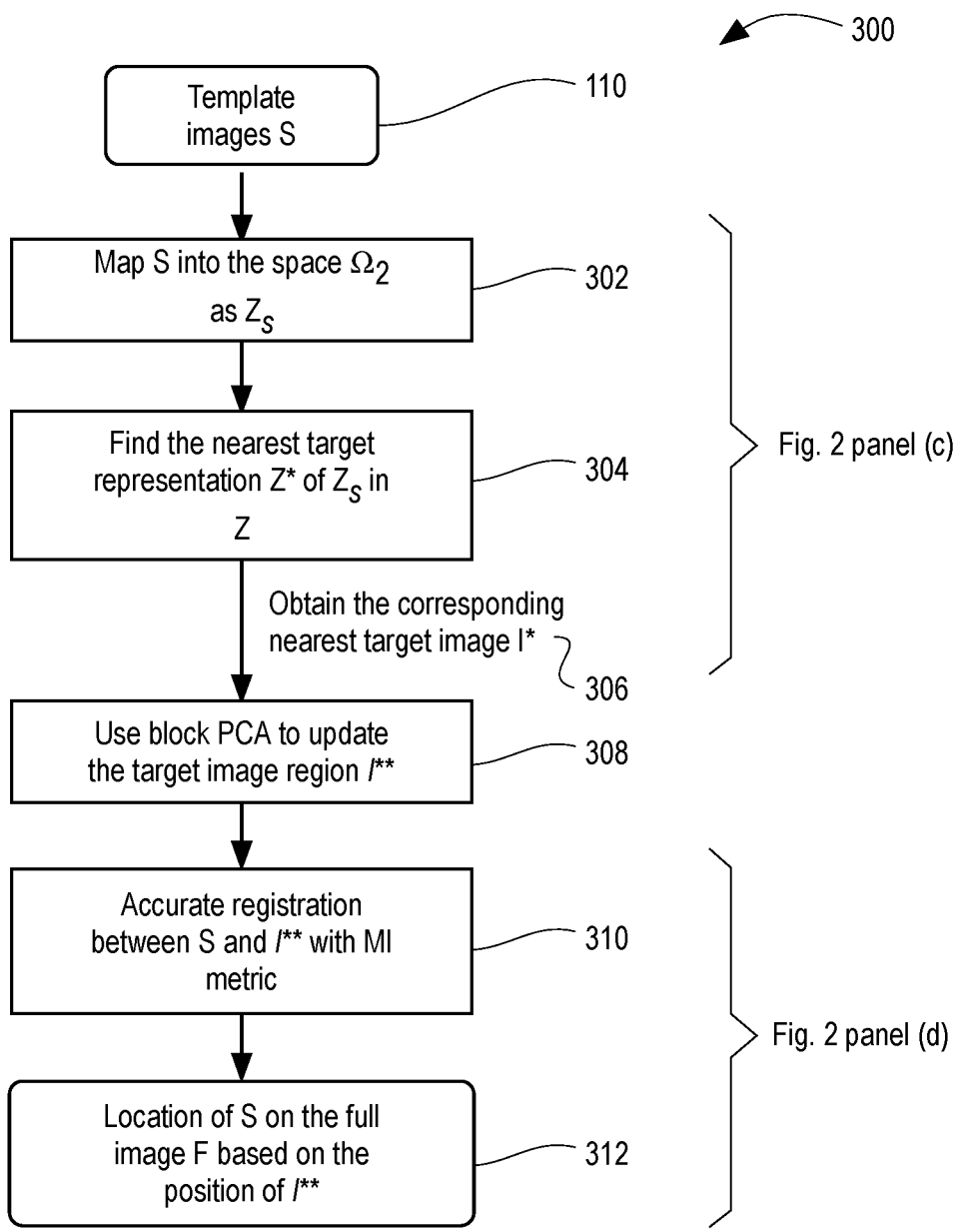
FIG. 4 is a flow chart of a sequence of processing instructions representing panels (c) and (d) of FIG. 2. These processing steps can be done in an "on-line" manner, i.e., at the time the template images are acquired. The processing steps can be executed in the device acquiring the template images (e.g., portable fundus camera, e.g., smartphone, etc.) or in a remote processing unit, such as a computer workstation in an eye clinic that receives the template images from the device the patient uses to acquire the template images.

With the above explanation in mind, attention will now be directed to FIGS. 3 and 4 and the steps of panels (a)-(d) described in further detail. FIG. 3 illustrates detailed steps 200 of the pre-processed part, referring to (a) and (b) panels in FIG. 2. The input is the large FOV full image F (100), which at step 202 is split or cropped into image patches (target images) $I_i$ with a certain offset, e.g., 10 pixels. At step 204, a dimensional reduction process (e.g., PCA) is performed to the target images mapping them into the low dimensional space (FIG. 2 panel (b)) and the output is the low-dimension representations Z of F's patches. PCA is used for the dimension reduction of images, generating the representations in a low dimension space. At step 206 this low dimension representation is saved in computer memory.

FIG. 4 illustrates the sequence of processing steps 300 for a template image, referring to (c) and (d) panels in FIG. 2. Together, they form a matching step of dimension reduction for the template image and registration using mutual information. The process has two steps, coarse localization (steps 302 and 304, FIG. 2 panel (c)) and accurate registration (steps 308, 310 and 312, FIG. 2 panel (d)). The input is the template images S to be matched (110), and the output is the mapped template on the full image F, after step 312 is performed. In step 302, S is mapped to the low dimensional space. At step 304, we find the nearest target representation in the low dimensional pace, 306. At step 308 we use block PCA to update the target image region to I. At step 310 we perform an accurate registration tween S and I with a MI metric. At step 312 we determine the location of the template image on the full image F based on the position of the updated target image region I**. A nearest target image I* of S on the full image is obtained in the coarse localization, and image I* and S have a large overlap. Block PCA is used to update I* to I on the full image F, getting more overlap with S. The template S can be matched on F based on the location of I.

A specific embodiment of our procedure of FIG. 2 used is set forth below.

1. FIG. 2, Panel (a): Create Target Images from the Full (Baseline) Image

We define the full image and template as F and S respectively. The full image F is split into target images $I_1$, $I_2$, ..., $I_N$:

$$I_i = \emptyset(b_i, F).$$

The function Ø crops the target images $I_i$ from F at b, and $b_i = [x_i, y_i, h, w]$, where $(x_i, y_i)$ denotes the center position and (h,w) denotes the width and height of the cropped image. There is a certain displacement, f of neighboring target images in the x and y axes. As shown in FIG. 2 panel (a), each target image has a large overlap with its neighbors. The overlap forms the redundancy of the data which can indicate the location distribution between each image and its neighbors. Applying dimension reduction techniques on such data, as explained below, we can obtain the low-dimensional distribution map of all target images.

Target images are resized to vectors and form the matrix $X \in \mathbb{R}^{n \times d}$.

2. FIG. 2 Panel (b): Create Low Dimensional Representations of the Target Images with PCA Dimension reduction methods allow the construction of low-dimensional summaries, while eliminating redundancies and noise in the data. To estimate the template location in the 2d space, the full image dimension is redundancy, thus we apply dimension reduction methods for the template coarse localization.

Generally, we can distinguish between linear and nonlinear dimension reduction techniques. The most prominent linear technique PCA. PCA is selected as the dimension reduction method in RetinaMatch since PCA is simple and versatile. Specifically, PCA forms a set of new variables as a weighted linear combination of the input variables. Consider a matrix $X=[x_1, x_2, \ldots, x_d]$ of dimension n×d, where n denotes the number of observations and d is the number of variables. Further, we assume that the matrix X is column-wise mean centered. The idea of PCA is to form a set of uncorrelated new variables (referred to as principal components) as a linear combination of the input variables:

$$z_i = Xw_i, \quad (1)$$

where $z_i$ is the $_i$th principal component (PC) and $w_i$ is the weight vector. The first PC explains most of the variation in the data, the subsequent PCs then account for the remaining variation in descending order. Thereby, PCA imposes the constraint that the weight vectors are orthogonal. This problem can be expressed compactly as the following minimization:

$$\text{minimize } \|X-ZW\|_F^2$$

subject to $W^T W = I$ where $\|.\|_F$ is the Frobenius norm. The weight matrix W that maps the input data to a subspace turns out to be the right singular vectors of the input matrix X. Often a low-rank approximation is desirable, e.g., we compute the k dominant PCs using a truncated weight matrix $W_k=[w_1, w_2, \ldots, w_k]$. k is some integer, such as 20.

PCA is generally computed by the singular value decomposition (SVD). Many algorithms have been developed to streamline the computation of the SVD or PCA for high-dimensional data that exhibits low-dimensional patterns, see J. N. Kutz, et al., *Dynamic mode decomposition: data-driven modeling of complex systems*. SIAM, 2016, vol. 149. In particular, tremendous strides have been made accelerating the SVD and related computations using randomized methods for linear algebra. See the references 24-31 cited in the manuscript portion of the priority U.S. provisional application. Since we have demonstrated high performance with less than 20 principal components, the randomized SVD is used to compute the principal components, improving the efficiency in this retinal mapping application for mobile device platforms (e.g., smartphone, tablet). The randomized algorithm proceeds by forming a sketch Y of the input matrix $$Y = X\Omega,$$

Where $\Omega$ is a d×l random test matrix, say with independent and identically distributed random standard normal entries. Thus, the l columns of Y are formed as a randomly weighted linear combination of the columns of the input matric, providing a basis for the column space of X. Note, that l is chosen to be slightly larger than the desired number of principal components. Next, we form an orthonormal basis Q using the QR decomposition Y=QR. Now, we use this basis matrix to project the input data matrix to low-dimensional space $$B = Q^T X.$$

This smaller matrix B of dimension l×d can then be used to efficiently compute the low-rank SVD and subsequently the dominant principal components. Given the SVD of $B=U\Sigma V^T$, we obtain the approximate principal components as $$Z = QU\Sigma = XV.$$

Here, U and V are the left and right singular vectors and the diagonal elements of $\Sigma$ are the corresponding singular values. The approximation accuracy can be controlled via additional oversampling and power iterations.

Referring again to panel (b) of FIG. 2, in our particular implementation, we obtain the low-dimensional distribution representation of the target image distribution by implementing PCA on X:

$$Z = XW,$$

Where $Z=[z_1, z_2, z_3, \ldots, z_N]^T \in \mathbb{R}$, $w \in \mathbb{R}^{d \times l}$ and $l \ll d$. The image space $\Omega_1$ is mapped to a low-dimensional space $\Omega_2$ with the mapping W. W and Z are saved in memory, in what we have called a "dictionary", D.

It is important to note that PCA is sensitive to outliers, occlusions, and corruption in the data. In ophthalmological imaging applications, there are several potential sources of corruption and outliers when imaging the full image, including blur, uncorrected astigmatism, inhomogeneous illumination, glare from crystalline lens opacity, internal reflections (e.g., from the vitreoretinal interface and lens), transient floaters in the vitreous, and shot noise in the camera. Further, there is often a trade-off between illumination and image quality, and there is strong motivation to introduce as little light as necessary for the patient comfort and health. The robust principal component analysis (RPCA) was introduced specifically to address this issue, decomposing a data matrix into the sum of a matrix containing low-rank coherent structure and a sparse matrix of outliers and corrupt entries. In general, RPCA is more expensive than PCA, requiring an iterative optimization to decompose the original matrix into sparse and low-rank components. Each step of the iteration is as expensive as regular PCA, and typically on the order of tens of iterations are required; however, PCA may be viewed as an offline step in our procedure, so that this additional computational cost is manageable. RPCA has been applied with success in retinal imaging applications to improve image quality. In the examples presented in this work, the data appears to have few enough outliers so that RPCA is not necessary, although it is important to keep RCPA as an option for data with outliers and corruption. Further details on RPCA are contained in the references cited in the manuscript portion of our prior provisional application.

3. FIG. 2 Panel (c): Coarse Localization—Find the Nearest Target Image in the Low-Dimensional Space Given a template S, the coarse position can be estimated by recognizing its nearest target image. The nearest target image in the image space $\Omega_1$ should also be the nearest representation of S in the lower dimensional space $\Omega_2$. Accordingly, we obtain the low-dimension feature $z_s$ of the template in $\Omega_2$:

$$z_s = sW,$$

where $s \in \mathbb{R}^d$ is the reshaped vector of template S. Let $\Delta(z_s, z)$ be the Euclidean distance between $z_s$ and a feature z in Z. $z^*$ is the nearest target feature of the source image S in $\Omega_2$:

$$z^* = \arg\min_z \Delta(z_s, z).$$

The corresponding target image location is used as the coarse location of S. Ideally, the difference between the coarse location and the ground truth in x and y axes should be less than f/2 pixels.

In one of the experiments we performed, PCA outperforms other non-linear dimension reduction methods, while the error is larger than f/2. The main reason is that the image degradation creates spurious features that contribute to the final classification. To reduce the influence of local features, we implement block PCA to further improve the accuracy of the coarse localization. By computing the PCA of different local patches in the template, the effect of local features, which cannot be located correctly, is reduced. This procedure is shown in FIG. 5. The input is the template S (110) and nearest target image I from coarse localization 102B. To reduce the effect of the local deformation in coarse localization, S and I are split into small patches respectively (step 402A, 402B) and PCA is applied on the small patches (steps 404, 406). Similar to the coarse localization, the nearest target patch is determined for each template patch (step 408). The average position of all chosen target patches is computed as new center position of I (step 410) and new position of I is updated (step 412).

Obtaining the nearest target image, we crop a larger image at the same position from the full image as the new target image I. In this way, the template can have more overlap with the new target image when there is a large offset between two images. We segment I and the template S into small patches with the cropping function $_{[<]BEGINITALO}$, where the patch size is smaller than the source image with the axial displacement of neighboring patches f. Similarly, all image patches from I are mapped into the low-dimensional space $\Omega_3$ with W. Let Z' denote the low-dimensional representation of the target image distribution. Each template patch is then mapped to the space with W'. The nearest target patch for each template patch is determined with the Euclidean distance as described before. We use the same weight for each region of the template for localization. Let $b_m$ be the mean of the coordinates of selected nearest target patches, which then represents the center of the template on I. Accordingly, the template location on the full image can be estimated and the region is cropped as the image Ŝ. We store the representation of each of the target image patches in lower dimensional space in memory, referred to as "dictionary" T. The accurate registration is then applied to the template S and image Ŝ. In this way the coarse localization provides an estimate of a good initial point for the accurate registration (panel (d) of FIG. 2).

In the implementation of the proposed coarse localization, the full (baseline) image is assumed to exist so the dictionary D and dictionary T for each target image can be built in advance. This is the pre-computed part as shown in FIG. 2 panels (a) and (b).

Figure 7:
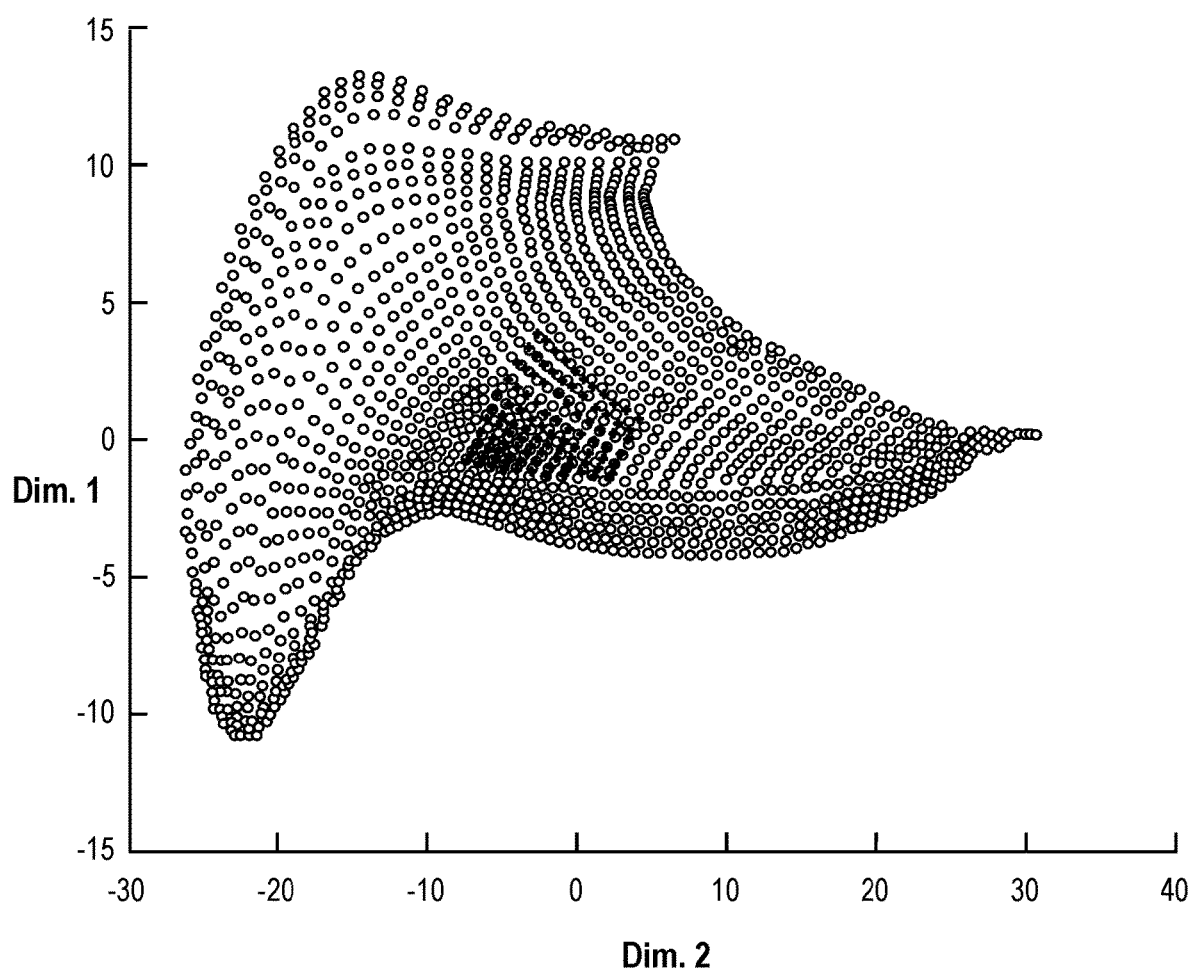
FIG. 7 is low dimensional representation of block PCA showing the mapping of template patches onto a target image patches using the procedure of FIG. 5. The T dictionary for each target image saves information of the open circled dots in the figure.

FIG. 7 is low dimensional representation of block PCA showing the mapping of template patches (represented by solid dots) onto a target image patches (represented by open circled dots) using the procedure of FIG. 5. The T dictionary for each target image saves information of the open circled dots in the figure.

Example processing instructions for coarse localization:

1. Map template S into space $\Omega_2$: $z_s = \tilde{s}W$.
2. Determine closest target image I with corresponding $z^*$: $z^* = \arg\min_z \Delta(z_s, z)$, $z^* \in Z$.
3. Segment S into $[S_p^1, S_p^2, \ldots, S_p^n]$: $S_p^i = \phi(b_i, S)$; Segment I into $[I_p^1, I_p^2, \ldots, I_p^n]$: $I_p^i = \phi(b_i, I)$.
4. Map target patches $I_p^i$ into space $\Omega_3$: $Z' = I_p W'$, where $I_p$ is formed with vectorized $I_p^i$.
5. For each template patch $S_p^i$:
6.   (i) Map $S_p^i$ into space $\Omega_3$: $\tilde{z}_s^i = S_p^i W'$.
7.   (ii) Determine its closest target patch $I_p^{Idx(i)}$ with index Idx(i).
8. $b_m = \frac{1}{n}\sum_{i=1}^n b_{Idx(i)}$, where $b_{Idx(i)}$ is the coordinate of selected target patch $I_p^{Idx(i)}$.
9. return localization region $\hat{S} = \phi(b_m, F)$).

4. FIG. 2 Panel (d) Accurate Registration and Location of Template onto Baseline Panel (d) of FIG. 2 includes two sub-steps: (1) image registration between the template image and the nearest target image, found in the procedure of FIG. 2 panel (c), and (2) locate the template onto the full (or baseline) image.

(1) Image Registration Between Template and Nearest Target Image Using Mutual Information (MI) (FIG. 4 step 310)

In this section, we describe the maximization of MI for multimodal image registration. We define images S and Ŝ as the template and target images, respectively. A transform u is defined to map pixel locations $x \in S$ to pixel locations in Ŝ.

The main idea of the registration is to find a deformation û at each pixel location x that maximizes the MI between the deformed template image $S(u(x))$ and the target image $\hat{S}(x)$. Accordingly, $$u_{opt} = \arg\min_u MI(S(u(x)), \hat{S}(x)),$$

Where $$MI(S(u(x)), \hat{S}(x)) = \sum_{i_1 \in S}\sum_{i_2 \in \hat{S}} p(i_1, i_2)\log\left(\frac{p(i_1, i_2)}{p(i_1)p(i_2)}\right).$$

Here, $i_1$ and $i_2$ are the image intensity values in $S(u(x))$ and $\hat{S}(x)$, respectively and $p(i_1)$ and $p(i_2)$ are their marginal probability distributions while $p(i_1, i_2)$ is their joint probability distribution. The probability distributions $p(i_1, i_2)$ reflect the degree to which the greyscale (image intensity) values of each pixel in $S(u(x))$ and $\hat{S}(x)$ are similar; $p(i_1, i_2)$ has a high value (closer to 1) if the pixel values are similar, and low value (closer to 0) if the pixel values are dissimilar. In more detail, in terms of mutual information, based on discrete data like images, each pixel has a grayscale value for 0 to 255. (Although examples herein may describe use of grayscale images for the fundus image work, embodiments are not so limited and may also employ color images as appropriate). We first compute the joint histogram of two images: the joint histogram will be 256×256, which counts the number of corresponding pixels' grayscale from two images. For example, if in the first pixel, one image has a grayscale of 100 and another one is 120, then the joint histogram map (100, 120) will add one. After we finished the joint histogram, the joint probability $p(i_1, i_2)$ can be obtained by normalizing the joint histogram. Then the marginal probability is computed according to:

$$P(i1) = \sum_{i2} P(i1, i2).$$

(2) Locate the Template onto the Full Image (FIG. 4 Step 312)

In this step images S and Ŝ are accurately registered with maximization of mutual information, as per sub-step (d)(1) above. The location of mage Ŝ on the full image F becomes the estimated displacement of the template S. In our work, the transform u for alignment is given as an affine transformation:

$$u = \begin{bmatrix} a_{11} & a_{12} & t_x \\ a_{21} & a_{22} & t_y \\ 1 & 1 & 0 \end{bmatrix}$$

It will be appreciated that the processing to create the target images and map them into lower dimensional space (panels (a) and (b) of FIG. 2) can be done off-line, e.g., in advance of receiving a set of template images from a patient. The processing of FIG. 2, panels (c) and (d) described above could be said to be "online", performed at the time of collecting the images in the portable fundus camera, or receiving the images from the patient's device at an eye clinic. Once the procedure of FIG. 2 has been performed and the template images matched to the baseline image, a mosaic of the entire retina can be created from the template images, and then the differences between the current retinal image mosaic and the baseline image ascertained from a comparison, e.g., in order to monitor the subject's health or check for onset, progression or improvement in eye disease (see the Applications section below).

Image Mosaicking

Figure 6:
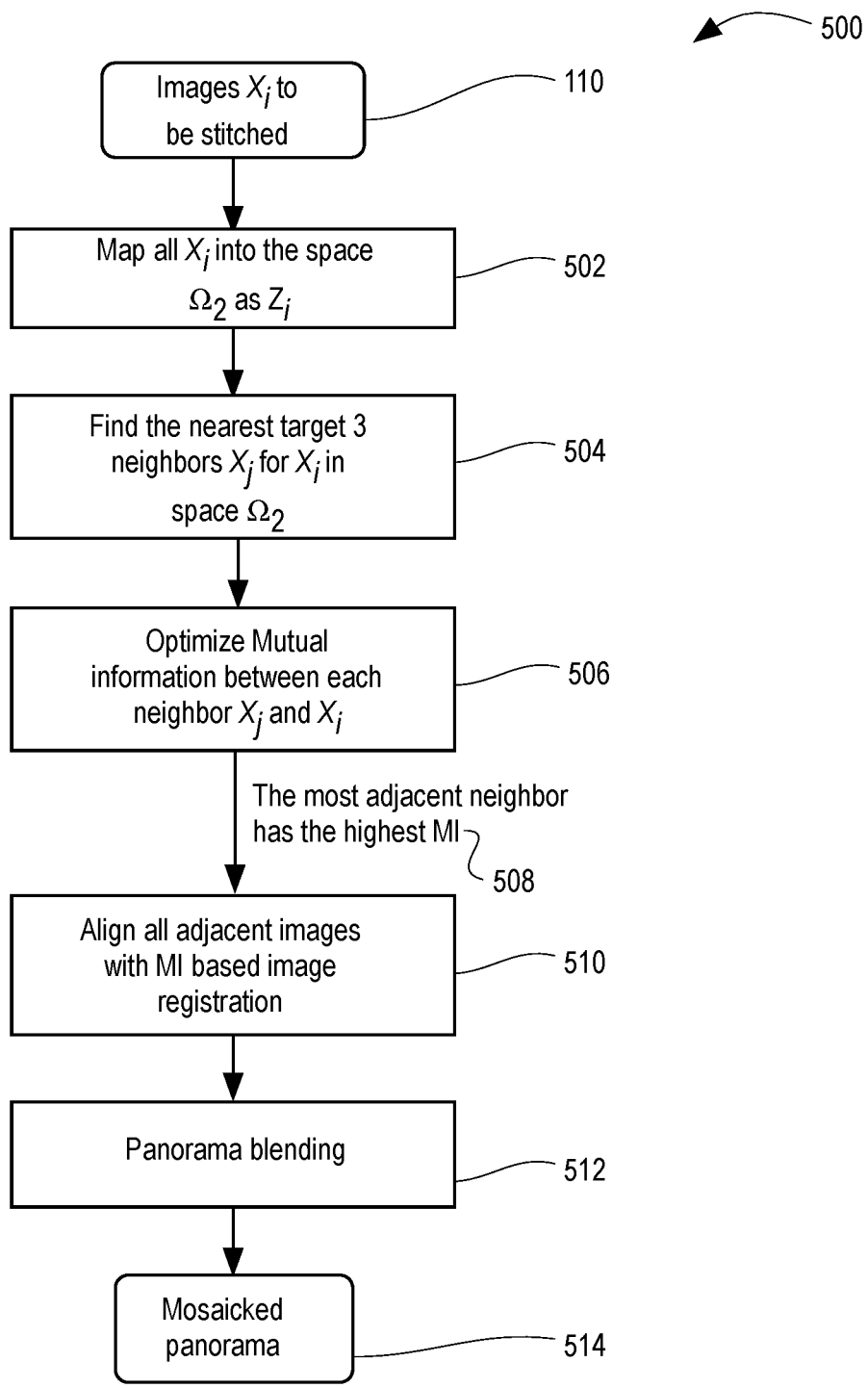
FIG. 6 is a flow chart of a sequence of processing instructions for constructing a mosaic or panorama of template images.

FIG. 6 illustrates an overview of a new image mosaicking method based on the dimension reduction idea. Given a series of images to be stitched (110), PCA can map them into a low dimensional space (step 502), where it is easy to find near images with overlap. The image registration method with MI metric is then applied to adjacent image pairs iteratively to stitch all images.

As pointed out previously, the full retina image can be stitched into a panorama by using many small templates. Users must capture a series of images in naturally unconstrained eye positions to explore different regions of the retina. It is problematic to determine adjacent images before the registration when we apply area-based registration approaches, because at that time they may not have effective descriptors for matching.

Related to the dimension reduction in the proposed template matching method, here we present the procedure shown in the table below to learn the positional relationship of images to be stitched. In this way, the adjacent images can be recognized and registered efficiently.

For a series of small images $X_i$, we form the matrix X. PCA is applied to X and returns the low-dimensional features for each image in $\Omega_2$. The distance between features in $\Omega_2$ indicates the distance between images. We find the nearest N (e.g., N=3) target neighbors in the low dimensional space. The nearest neighbor of image $X_i$ is the one with largest overlap; the image pair is then registered with MI-based approach. To improve the algorithm robustness, the first N nearest neighbors for each image are first selected to compute MI with, and we keep the one with the largest metric value. The above procedure can be represented in the following pseudocode.

Processing instructions: Image stitching (with reference to FIG. 6)
  1 Map images into space $\Omega_2$: Z=XW. (step 502)
  2 For each image $X_i$:
  3 (i). Find the nearest N (e.g., N=3) neighbors minimizing the feature distance $\Delta(Z_i,Z_j)$. (step 504)
  4 (ii). Compute the Mutual Information between each $X_j$ and $X_i$ and take the adjacent image with highest MI. (step 506, 508)
  5 Panorama R Mosaicking: Align all the adjacent images with mutual information based registration method. (step 510)
  6 Panorama blending. (step 512)
  7 return mosaicked panorama R. (step 514)

Applications

Our method of template matching with baseline images and image mosaicking allows for longitudinal comparisons with previously obtained fundus images of the patient. Such longitudinal comparisons have several applications in the field of ophthalmology as will be described below. Such applications are examples of how the methods of this disclosure can be practiced in a teleophthalmology setting. Other suitable applications are also supported by the embodiments described herein, including options outside of the field of retinal template matching.

Hypertension

In the retinal symptom of hypertension, the larger arteries constrict and the venous vessels enlarge in diameter. Ophthalmologists can select several detection points on the vessels. With the captured images coming from the patient as per FIG. 1, we construct a mosaic image of the fundus and can detect those images which cover the selected detection points. Then, the vessel width at the select points can be compared with the previous state by making measurements of vessel width and comparing them with previously stored fundus images of the patient. For more precise vessel width measurement, our method of FIG. 2 can be combined with vessel segmentation. The vessel width corresponding to each selected point is obtained by segmentation around the mapped location. The vessel segmentation here then is applied on very small retina patches around the point, which is more robust and accurate than segmentation of wide FOV retina images.

Abusive Head Trauma

The biomarkers of abusive head trauma (AHT) is another example. The most common retinal manifestation of AHT is multiple retinal hemorrhages in multiple layers of the retina. Matching the captured images onto the full retina image, the hemorrhagic spots can be easily segmented after the subtraction of the current retina regions and previous status. The AHT then can be recognized automatically when such spots are detected. This method permits identification of AHT from images obtained with portable fundus cameras.

Diabetic Retinopathy

The obvious symptoms of diabetic retinopathy (DR) are retina hemorrhages and the presence of exudate. They can be monitored follow the similar process of AHT screening.

Glaucoma

Glaucoma can cause the optic nerve cup to enlarge. Our matching method can automatically select the images that cover the optic nerve. The following segmentation can be easily implemented and a computation of the optic cup diameter performed. Enlargement of the optic nerve cup over time can be ascertained by comparing the computations from a current image with an image from a previous point in time.

Use RetinaMatch as a General Image Template Matching Method

Besides the retina images, the technique of RetinaMatch can be used in other type of image template matching tasks. Note that our method of FIG. 2 does not use the specific features of retina. Rather, our method is a combination of coarse localization and accurate localization based on MI. The accurate localization can be replaced by any other existing image registration method, and the coarse localization can always reduce the error caused by the small template size and sparse image features. Thus, the procedure of FIG. 2 is generally applicable to the problem of matching small field of view images to a previously obtained wide field of view image.

Use RetinaMatch for Camera Localization

Having the image of the full view, our method of FIG. 2 can be used for camera localization when matching the captured field of view onto the full or baseline image. In the case of endoscopic guidance of therapy by a surgical robot, the current limited-sized FOV can be matched onto the panorama for endoscope localization. Thus, this image template matching technique can be used to create a more reliable closed-loop control for the robot arm and surgical tool guidance. For example, after registering the template images the resulting mosaicked image can be inspected, e.g., to locate a surgical tool in the eye.

Augmented Reality (AR), Eye Glasses, Etc. And Monitoring Changes Over Time

A retinal imaging system (e.g., consumer grade camera with ancillary imaging device, e.g., D-eye) can be portable and further, can be worn as integrated into, for example, glasses, or an Augmented Reality (AR), Virtual Reality (VR) and/or Mixed Reality (MR) headset, allowing a series of images to be taken and analyzed, either daily, weekly, monthly, or when the user or ophthalmologist requests. These measurements can be discrete, continual, but in a time series and analyzed longitudinally over the increasing time period. Change in a retina can detected by registering and comparing the captured small FOV images to a full baseline retina image using our template matching method.

AR, VR and/or MR devices can be used to optically scan the retina to form images and thereby acquire the template images. Even more pragmatically, spectacles or sunglasses can be used because of the smaller size, lower costs, and increasing utility to the user. A scanned light beam entering the pupil of the eye and striking the retina to form video rate images perceived by the user's brain can also be used to acquire images of high contrast structures, such as the vasculature containing blood.

A device can operate without major changes in performance during its lifetime and can be used as a monitor of the condition of a user's eye. By comparing retinal images from such a device over time, the changes in the user's optical system (such as cornea, intraocular lens, retina, and liquid environments) can be monitored to alert the user in possible health changes. For example, these changes can be gradual, like increasing light scattering from the crystalline or intraocular lens due to cataract formation, or the appearance and structural changes in the retina due to diabetic retinopathy. In addition, chronic diseases which may have variations over time in the blood vessel size and shape in conditions of hypertension are another example. Acute changes such as bleeding within the retinal can indicate brain trauma. Relative and repeatable changes in number, size, and shape of structures in the retinal images may indicate that the measured change is due to a particular disease type and not that the AR, VR, MR, glasses, or other type of monitoring device has slowly or suddenly changed its imaging performance or has become unstable.

However, in many healthy users the optical system will be unchanging over time. In this case, the vasculature of the retina can be used as a test target for detecting optical misalignments, focus errors, light scanning errors and distortions, non-uniform and color imbalance in the illumination, and aberrations in the imaging system. This situation can occur if the monitoring device, such as an AR, VR, or MR device is degraded due to mechanical impact, breakage, applied stresses, applied vibration, thermal changes, and opto-electrical disruption or interference. These changes can be observed in a measurable change to the current retinal images compared to before these changes happened to the AR, VR or MR device. Retinal vasculature images can be used to measure the level of image distortion within an imaging system by resolving a specific pattern of high contrast lines. By processing the retinal images or their panoramic mosaic into binary (black and white) high contrast by intensity thresholding and/or segmentation, the vascular network can be made into a RetinaTest Target.

By measuring the change in the images of the RetinaTest Target before and after a change in performance of the AR, MR or MR device, a calibration measurement of imaging performance can be made dynamically. This calibration measurement can be transmitted to a local computing device or to a remote location for analysis and diagnosis of the change of performance of the AR, VR or MR device. Furthermore, the calibration measurement can be updated when corrective actions are implemented within the AR, VR or MR device which can be used in a feedback loop as an error signal for the purpose of regaining optimal performance of the AR, VR or MR device. Since the blood has a distinct optical absorption spectrum in the arteries and veins and scattering differences can be determined, the calibrated imaging performance should be performed across the spectral range of visible to near infrared wavelengths being used by the AR, VR or MR device.

Gaze Tracking

The acquisition of template images and registration onto a baseline image as described above can be further used to determine the gaze position the user. In particular, as the user's gaze changes position, the angle between the optical axis of the camera and the fovea or other structures at the back of the eye will change accordingly, and by measuring the shift in this angle the gaze position can be determined.

While the above discussion has been directed primarily to detecting changes in the retina and monitoring for change, progression, occurrence etc. of eye disease, more generally the present methods can be used to monitor for other conditions (e.g., diabetes, etc.) that are not retinal conditions per se, but that may be measured in the retina. Furthermore, our methods can be also used to monitor improvement in a condition of the retina, for example, monitor effectiveness of a treatment or therapy, in addition to detecting onset or worsening of disease.

Other applications are of course possible as would be apparent to one skilled in the art.

The manuscript portion of our priority US provisional application includes data regarding experiments we conducted using our template matching method, including validation on a set of simulated images from the STARE dataset, and in-vivo templated images captured from the D-eye smartphone device matched to full fundus images and mosaicked full images. The interested reader is directed to that portion of the provisional application for further details.

As used in the claims, the term "head-worn retinal imaging device" is intended to refer broadly to any device worn or supported by the head which includes a detector or camera and associated optical components designed for imaging the retina, including but not limited to glasses, and augmented, mixed or virtual reality headsets. As another example, devices which include scanned light (from laser or LED) display using a near-infrared (NIR) wavelength can also be a camera with the addition of a fast NIR detector, and such a device could be adapted as a head-worn retinal imaging device.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular. Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, refer to this application as a whole and not to any particular portions of the application.

What is claimed is:

1. A method for monitoring a retina of a subject, comprising the steps of:
    obtaining a set of retina template images of a retina;
    matching a retina template image in the set to a retina baseline image of the retina at least by:
        applying dimension reduction to the retina baseline image and the retina template image; and
        generating a registered retina template image at least by registering the retina template image to at least a portion of the retina baseline image, wherein the retina baseline image captures a wider field of view than the retina template image; and
        registering the retina template image as a registered retina template image at least based at least in part upon at least a portion of the retina baseline image, wherein the retina baseline image comprises a wider field of view than the retina template image; and
    detecting a change in a characteristic pertaining to the retina or a subject of the retina based at least in part upon a comparison between the registered retina template image and the retina baseline image.

2. The method of claim 1, matching the retina template image to the retina baseline image comprising:
    generating a plurality of smaller offset target images at least by cropping the retina baseline image, wherein at least two of the plurality of smaller offset target images overlap each other.

3. The method of claim 2, matching the retina template image to the retina baseline image comprising:
    mapping a smaller offset target image of the plurality of smaller offset target images into a lower-dimensional space based at least in part upon a first result of a principal component analysis performed on the plurality of smaller offset target images, where the lower-dimensional space has a smaller dimensionality than a dimensional space of the retina baseline image.

4. The method of claim 3, matching the retina template image to the retina baseline image further comprising:
    performing coarse localization on the retina template image or the set of retina template images based at least in part upon the principal component analysis performed on the retina template image based at least in part upon a first result of the principal component analysis.

5. The method of claim 4, matching the retina template image to the retina baseline image further comprising:
    determining a nearer target image based at least in part upon a result of performing the coarse localization to the retina template image or the set of retina template images.

6. The method of claim 5, matching the retina template image to the retina baseline image further comprising:
    determining a displacement parameter in a domain of a mutual information metric for registration of the retina template image with the nearer target image based at least in part upon the principal component analysis performed on the retina template image.

7. The method of claim 6, matching the retina template image to the retina baseline image further comprising:
    initializing metric processing on the mutual information metric at least by using at least the displacement parameter; and
    registering the retina template image with the nearer target image based at least in part upon mutual information registration and a location of the retina template image onto the retina baseline image.

8. The method of claim 7, matching the retina template image to the retina baseline image further comprising:
    after the retina template image is registered with the nearest target image, locating the retina template image onto the retina baseline image.

9. The method of claim 1, further comprising updating the retina baseline image with a mosaic image having the set of retina template images registered to the retina baseline image, wherein the imaging capturing device comprises a head-worn retinal imaging device, a fundus camera which further includes an optical coherence tomography (OCT) component, a portable scanning laser ophthalmoscope, a hand-held device including a camera adapted for imaging the retina, or a camera embodied in a smartphone or tablet computer configured with apparatus to assist in taking an image of the retina.

10. The method of claim 1, wherein the change in the characteristic of the retina or the subject comprises hypertension, abusive head trauma, diabetic retinopathy, or glaucoma.

11. The method of claim 1, further comprising:
mosaicking the retina template image into a new retina baseline image;
determining a separate set of retina template images;
comparing the separate set of retina template images with the new retina baseline image to generate a comparison result; and
determining whether the characteristic pertaining to the retina or the subject has degraded based at least in part upon the comparison result.

12. The method of claim 11, mosaicking the retina template image comprising:
determining a set of smaller images for the retina template image; and
mapping the set of smaller images into a mapped set of smaller images in a lower-dimensional space based at least in part upon a principal component analysis, wherein the lower-dimensional space has a lower dimensionality than a separate dimensional space of the retina template image.

13. The method of claim 12, mosaicking the retina template image comprising:
generating a set of lower-dimensional features in the lower-dimensional space for the retina template based at least in part upon the mapped set of smaller images;
determining a distance metric between two lower-dimensional features in the set of lower-dimensional features in the lower-dimensional space;
determining, for a smaller image of the set of smaller images, one or more closer target images in the lower-dimensional space based at least in part upon an extent of overlap between a pair of the smaller image and a closer target images of the one or more closer target images; and
determining a mutual information metric for the pair of the smaller image and the closest target image.

14. The method of claim 13, mosaicking the retina template image comprising:
registering, for the smaller image, the one or more closest target images based at least in part upon the mutual information metric; and
generating a stitched image at least by aligning the one or more closest target images with at least the mutual information metric.

15. An extended reality device, comprising:
an imaging device;
a processor operatively coupled to the imaging device; and
a memory storing therein a sequence of instructions which, when executed by the processor, causes the processor to perform a set of acts, the set of acts comprising:
obtaining a set of retina template images of a retina;
matching a retina template image in the set to a retina baseline image of the retina at least by:
applying dimension reduction to the retina baseline image and the retina template image; and
generating a registered retina template image at least by registering the retina template image to at least a portion of the retina baseline image, wherein the retina baseline image captures a wider field of view than the retina template image; and
registering the retina template image as a registered retina template image at least based at least in part upon at least a portion of the retina baseline image, wherein the retina baseline image comprises a wider field of view than the retina template image; and
detecting a change in a characteristic pertaining to the retina or a subject of the retina based at least in part upon a comparison between the registered retina template image and the retina baseline image.

16. The extended reality device of claim 15, wherein the set of acts further comprising:
generating a plurality of smaller offset target images at least by cropping the retina baseline image, wherein at least two of the plurality of smaller offset target images overlap each other;
mapping a smaller offset target image of the plurality of smaller offset target images into a lower-dimensional space based at least in part upon a first result of a principal component analysis performed on the plurality of smaller offset target images, where the lower-dimensional space has a smaller dimensionality than a dimensional space of the retina baseline image; and
performing coarse localization on the retina template image or the set of retina template images based at least in part upon the principal component analysis performed on the retina template image based at least in part upon a first result of the principal component analysis.

17. The extended reality device of claim 15, wherein the set of acts further comprising:
mosaicking the retina template image into a new retina baseline image;
determining a separate set of retina template images;
comparing the separate set of retina template images with the new retina baseline image to generate a comparison result;
determining whether the characteristic pertaining to the retina or the subject has degraded based at least in part upon the comparison result;
determining a set of smaller images for the retina template image; and
mapping the set of smaller images into a mapped set of smaller images in a lower-dimensional space based at least in part upon a principal component analysis, wherein the lower-dimensional space has a lower dimensionality than a separate dimensional space of the retina template image.

18. A non-transitory machine accessible storage medium having stored thereupon a sequence of instructions which, when executed by a processor of a mixed reality device, causes the processor to perform a set of acts, the set of acts comprising:
obtaining a set of retina template images of a retina;
matching a retina template image in the set to a retina baseline image of the retina at least by:
applying dimension reduction to the retina baseline image and the retina template image; and
generating a registered retina template image at least by registering the retina template image to at least a portion of the retina baseline image, wherein the retina baseline image captures a wider field of view than the retina template image; and
registering the retina template image as a registered retina template image at least based at least in part upon at least a portion of the retina baseline image, wherein the retina baseline image comprises a wider field of view than the retina template image; and
detecting a change in a characteristic pertaining to the retina or a subject of the retina based at least in part upon a comparison between the registered retina template image and the retina baseline image.

19. The non-transitory machine accessible storage medium of claim 18, wherein the set of acts further comprising:
generating a plurality of smaller offset target images at least by cropping the retina baseline image, wherein at least two of the plurality of smaller offset target images overlap each other;
mapping a smaller offset target image of the plurality of smaller offset target images into a lower-dimensional space based at least in part upon a first result of a principal component analysis performed on the plurality of smaller offset target images, where the lower-dimensional space has a smaller dimensionality than a dimensional space of the retina baseline image; and
performing coarse localization on the retina template image or the set of retina template images based at least in part upon the principal component analysis performed on the retina template image based at least in part upon a first result of the principal component analysis.

20. The non-transitory machine accessible storage medium of claim 18, wherein the set of acts further comprising:
mosaicking the retina template image into a new retina baseline image;
determining a separate set of retina template images;
comparing the separate set of retina template images with the new retina baseline image to generate a comparison result;
determining whether the characteristic pertaining to the retina or the subject has degraded based at least in part upon the comparison result;
determining a set of smaller images for the retina template image; and
mapping the set of smaller images into a mapped set of smaller images in a lower-dimensional space based at least in part upon a principal component analysis, wherein the lower-dimensional space has a lower dimensionality than a separate dimensional space of the retina template image.

* * * * *